US00PP27143P3

(12) United States Plant Patent
Zaiger et al.

(10) Patent No.: US PP27,143 P3
(45) Date of Patent: Sep. 13, 2016

(54) NECTARINE TREE NAMED 'AUGUST CHIEF'

(50) Latin Name: ***Prunus persica* var. *nucipersica***
Varietal Denomination: August Chief

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 104 days.

(21) Appl. No.: 14/544,565

(22) Filed: Jan. 23, 2015

(65) Prior Publication Data

US 2016/0219771 P1 Jul. 28, 2016

(51) Int. Cl.
*A01H 5/08* (2006.01)

(52) U.S. Cl.
USPC ..... Plt./190

(58) Field of Classification Search
USPC ..... Plt./187, 190
See application file for complete search history.

*Primary Examiner* — Susan McCormick Ewoldt

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size fruit.
3. Fruit having a high degree of attractive red skin color.
4. Fruit with very good mild, sweet, sub-acid flavor.
5. Firm, yellow flesh fruit with good shipping quality.

1 Drawing Sheet

Botanical designation: *Prunus persica* var. *nucipersica*.
Variety denomination: 'August Chief'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

2. Prior Varieties

Among the existing varieties of nectarine trees, which are known to us, and mentioned herein, 'Honey Kist' Nectarine (U.S. Plant Pat. No. 9,333), 'Honey Diva' Nectarine (U.S. Plant Pat. No. 15,291) and the proprietary non-patented nectarine seedling selections '25LD605', '41GF131' and '63EC416'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was originated by us in our experimental orchard located near Modesto, Calif. as a first generation cross between our proprietary non-patented nectarine seedling selections with the field identification numbers '25LD605' and '41GF131'. The proprietary non-patented nectarine seed parent '25LD605' originated as an open pollinated seedling selection from 'Honey Kist' Nectarine (U.S. Plant Pat. No. 9,333). The proprietary non-patented nectarine pollen parent '41GF131' originated as an open pollinated seedling selection from our proprietary non-patented nectarine seedling '63EC416'. We planted and maintained a large number of these first generation seedlings on their own root system. Under close and careful evaluation we recognized the desirable tree and fruit characteristics of the present variety and selected it in 2000 for additional asexual propagation and commercialization.

ASEXUAL REPRODUCTION OF THE VARIETY

In 2000 asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The present new variety of nectarine tree (*Prunus persica* var. *nucipersica*) is of large size, vigorous, upright growth and a regular and productive bearer of large size, yellow flesh, clingstone fruit. The fruit is further characterized by having a mild, sweet, sub-acid flavor with very good eating quality. In comparison to its seed parent '25LD605' nectarine (non-patented) the fruit of the new variety is larger in size and is approximately 52 days later in maturity. In comparison to its non-patented nectarine pollen parent '41GF131' the fruit of the new variety is approximately 5 weeks earlier in maturity. In comparison to the commercial variety 'Honey Diva' Nectarine (U.S. Plant Pat. No. 15,291) the fruit of the new variety is larger in size and is approximately 6 days earlier in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 14 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 14 year old specimens grown near Modesto, Calif., with color in accordance with Munsell Book of Color published in 1958.

Tree:

*Size.*—Large, usually pruned to 3 to 3.5 meters in height and width for economical harvesting of fruit. Size varies with different cultural practices.

*Vigor.*—Vigorous, growth of 1.5 to 2 meters in height the first growing season. Varies with soil type, fertility of soil and climatic conditions.

*Form.*—Upright, usually pruned to vase shape.

*Branching habit.*—Upright, crotch angle approximately 35°, increases with heavy crop load.

*Productivity.*—Productive, thinning and spacing of fruit necessary for desired market size. Fruit set varies with climatic conditions during bloom time.

*Bearer.*—Regular, adequate fruit set 12 consecutive years. No alternate bearing observed.

*Fertility.*—Self-fertile.

*Density.*—Medium dense, usually pruned to vase shape to allow more sunlight to center of tree to enhance fruit color and health of fruit wood.

*Hardiness.*—Hardy in all stone fruit growing areas of California. Tree grown in USDA Hardiness Zone 9. Winter chilling requirement approximately 850 hours at or below 45° F.

Trunk:

*Size.*—Large. Average circumference 53.3 cm at 25.4 cm above ground on a 14 year old tree.

*Stocky.*—Medium stocky.

*Texture.*—Medium shaggy, roughness increases with age.

*Color.*—Varies from 10YR 5/2 to 10YR 3/4.

Branches:

*Size.*—Large. Average circumference 19.8 cm at 1.2 meters above ground. Crotch angle approximately 35°, increases with heavy crop load.

*Surface texture.*—New growth relatively smooth. Mature growth medium rough, roughness increases with age.

*Lenticels.*—Average number 14 in a 25.8 square cm section. Average length 5.5 mm. Average width 1.7 mm. Color varies from 7.5YR 5/10 to 10YR 6/12.

*Color.*—New growth varies from 2.5GY 5/8 to 10YR 4/8. Mature growth varies from 7.5YR 3/6 to 7.5YR 2/4, varies with age of growth.

Leaves:

*Size.*—Large. Average length 163.7 mm. Average width 45.3 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins. Lower surface relatively smooth, except for small ridges created by midrib and pinnate venation. Both upper and lower surfaces glabrous.

*Petiole.*—Average length 11.2 mm. Average width 1.9 mm. Longitudinally grooved. Surface — glabrous. Color varies from 5GY 5/8 to 5GY 4/6.

*Glands.*—Type — reniform. Size — large. Average length 1.4 mm. Average diameter 1.1 mm. Number varies from 2 to 6, average number 3. Located primarily on the base of leaf blade and upper portion of the petiole. Color varies from 5GY 5/8 to 5GY 4/8.

*Stipules.*—Average number 2. Average length 14.4 mm. Edges — pectinate. Color varies from 2.5GY 6/8 to 5GY 5/8.

*Color.*—Upper surface varies from 5GY 4/8 to 7.5GY 3/6. Lower surface varies from 5GY 4/6 to 5GY 3/6. Midvein color varies from 5GY 7/6 to 5GY 7/8.

Flower buds:

*Size.*—Large. Average length 16.7 mm. Average diameter 9.4 mm.

*Hardiness.*—Hardy with respect to California winters.

*Form.*—Conical, becoming elongated just before opening.

*Pedicel.*—Average length 2.9 mm. Average width 1.5 mm. Color varies from 2.5GY 6/8 to 5GY 6/8. Surface glabrous.

*Density.*—Light to medium.

*Color.*—Varies from 5RP 7/10 to 7.5RP 7/8.

Flowers:

*Blooming period.*—Date of First Bloom Feb. 16, 2014. Date of Petal Fall Feb. 26, 2014, varies slightly with climatic conditions.

*Size.*—Large, showy. Average height 20.0 1.6 mm. Average diameter 35.6 mm.

*Petals.*—Normally 5, alternately arranged to sepals. Size — large. Average length 20.1 mm. Average width 15.9 mm. Form — elliptical. Petal apex — rounded. Petal base — acuminate. Arrangement — overlapping. Margin — sinuate. Color varies from 5RP 8/4 to 5RP 6/8, fades with age of flower.

*Sepals.*—Normally 5, alternately arranged to petals. Size — medium to large. Average length 5.6 mm. Average width 5.1 mm. Shape — ovate, apex rounded. Margin — entire. Surface — upper surface glabrous, lower surface pubescent. Color — upper surface varies from 2.5GY 5/8 to 5GY 5/6. Lower surface varies from 5R 3/4 to 5R 2/6.

*Stamens.*—Average number per flower 45. Average filament length 14.5 mm. On average, the stamens are even with the height of the petals. Filament color varies from N 9.5/(white) to 5RP 4/6. Anther color varies from 7.5Y 8.5/6 to 7.5R 3/8.

*Pollen.*—Self-fertile. Color varies from 5Y 8.5/10 to 5Y 8.5/12.

*Pistil.*—Number — normally 1. Average length 16.6 mm. Position of stigma an average of 1.4 mm below anthers. Surface — glabrous. Color varies from 10Y 7/8 to 10Y 7/10.

*Fragrance.*—Slight aroma.

*Color.*—Varies from 5RP 8/4 to 5RP 8/6.

*Pedicel.*—Average length 3.7 mm. Average width 1.4 mm. Color varies from 2.5GY 6/8 to 5GY 6/8. Surface glabrous.

*Number flowers per flower bud.*—Normally one.

Fruit:

*Maturity when described.*—Firm ripe and ready for consumption.

*Date of first picking.*—Aug. 7, 2014.

*Date of last picking.*—Aug. 17, 2014, varies slightly with climatic conditions.

*Size.*—Large. Average diameter axially 73.7 mm. Average transversely in suture plane 79.8 mm. Average weight 267.0 grams, varies slightly with fertility of the soil, amount of thinning and climatic conditions.

*Form.*—Globose.

*Suture.*—Slightly lipped.

*Ventral surface.*—Smooth to slightly lipped.

*Apex.*—Slightly retuse.

*Base.*—Flat to slightly retuse.

*Stem cavity.*—Rounded to slightly elongated in suture plane. Average depth 6.3 mm. Average diameter 12.2 mm.

Stem:

*Size.*—Small to medium. Average length 9.4 mm. Average diameter 4.0 mm.

*Color.*—Varies from 7.5Y 6/10 to 10Y 6/6.

Flesh:

*Ripens.*—Evenly.

*Texture.*—Firm, meaty, crisp.

*Fibers.*—Few, small, tender.

*Firmness.*—Firm, comparable to other commercial nectarine varieties.

*Aroma.*—Slight.

*Amydgalin.*—Undetected.

*Eating quality.*—Very good.

*Flavor.*—Very good, with a mild, sweet, sub-acid flavor.

*Juice.*—Moderate amount, enhances flavor.

*Acidity.*—Not available.

*Brix.*—Average Brix 16.0°, varies slightly with amount of fruit per tree and climatic conditions.

*Color.*—Varies from 2.5Y 8.5/12 to 5Y 8/10.

*Pit cavity.*—Average length 38.3 mm. Average width 30.3 mm. Average depth 13.4 mm. Color varies from 2.5Y 8/10 to 7.5R 3/10.

Skin:

*Thickness.*—Medium.

*Surface.*—Smooth.

*Pubescence.*—Wanting.

*Tendency to crack.*—None.

*Color.*—Ground color varies from 5Y 8/8 to 5Y 8/10. Overspread with 7.5R 3/10 to 7.5R 2/8.

*Tenacity.*—Tenacious to flesh.

*Astringency.*—Undetected.

Stone:

*Type.*—Clingstone, strong adherence to flesh.

*Size.*—Large. Average length 37.3 mm. Average width 29.3 mm. Average thickness 24.7 mm.

*Form.*—Ovoid.

*Base.*—Flat.

*Apex.*—Pointed. Average length 2.7 mm.

*Surface.*—Pitted throughout, pits vary from round to elongated.

*Sides.*—Unequal, one side extending further from suture plane.

*Ridges.*—Relatively smooth, narrow ridges extending from base toward apex.

*Tendency to split.*—None.

*Color.*—Varies from 7.5YR 3/4 to 10R 2/6 when dry.

Kernel:

*Size.*—Large. Average length 17.9 mm. Average width 12.5 mm. Average depth 6.6 mm.

*Form.*—Ovoid.

*Viability.*—Viable, complete embryo development.

*Skin color.*—Varies from 5GY 9/6 to 5Y 8/8.

Use: Dessert. Market — local and long distance.

Keeping quality: Good, held firm in cold storage at 38° to 42° F. for 2 weeks without internal breakdown of flesh or appreciable loss of flavor.

Shipping quality: Good, minimal, skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree, (*Prunus persica* var. *nucipersica*) substantially as illustrated and described.

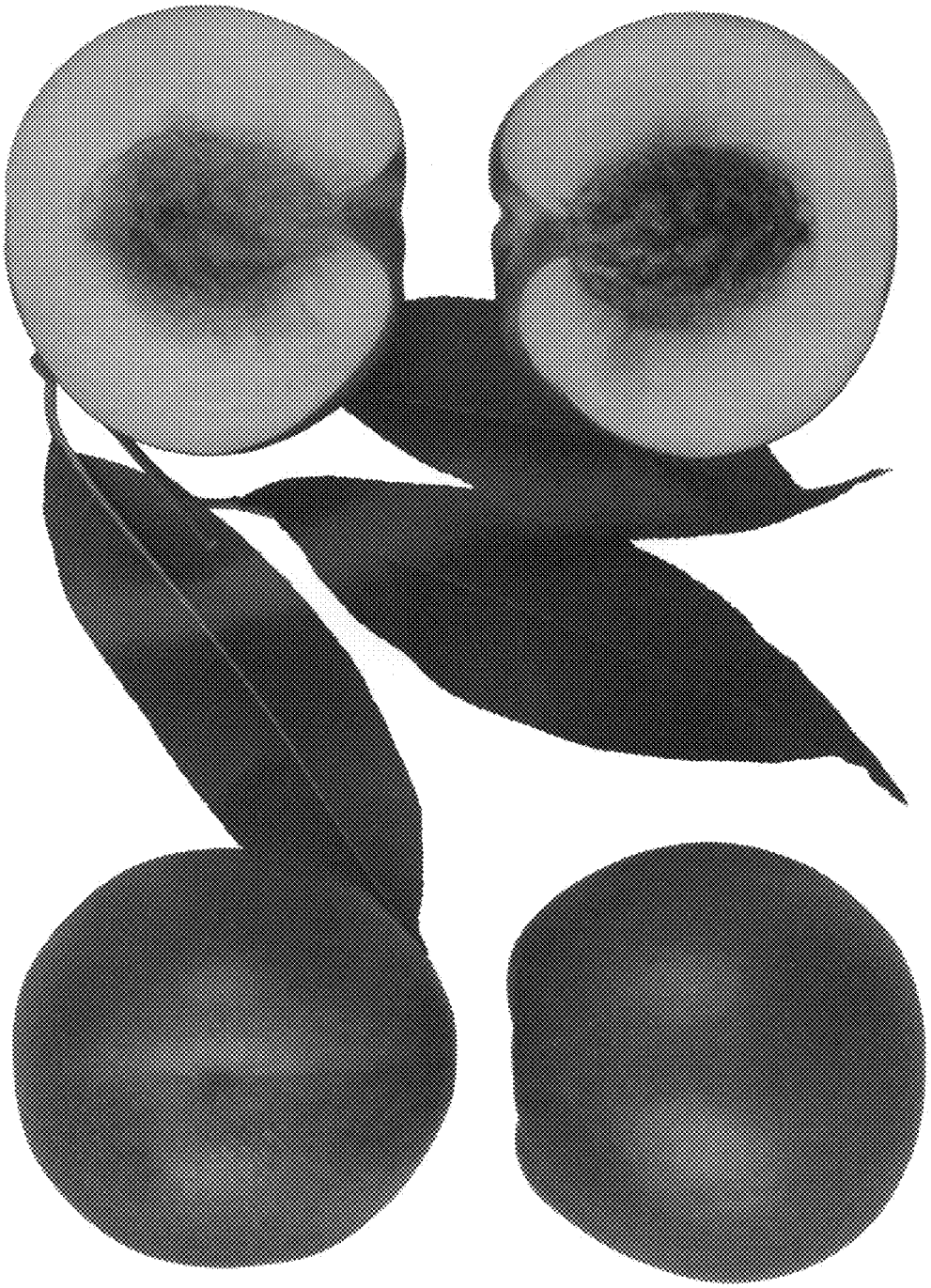

* * * * *